United States Patent [19]

Farng et al.

[11] Patent Number: 4,956,105

[45] Date of Patent: Sep. 11, 1990

[54] LUBRICANT COMPOSITION CONTAINING PHENOLIC/PHOSPHORODITHIOATE BORATES AS MULTIFUNCTIONAL ADDITIVES

[75] Inventors: Liehpao O. Farng, Lawrenceville; Andrew G. Horodysky, Cherry Hill, both of N.J.

[73] Assignee: Mobil Oil Corporation, New York, N.Y.

[21] Appl. No.: 200,345

[22] Filed: May 31, 1988

[51] Int. Cl.$^5$ ............... C10M 105/12; C10M 105/72; C10M 105/74

[52] U.S. Cl. ........................ 252/32.7 E; 252/32.5; 252/32.7 R

[58] Field of Search ............ 252/32.7 E, 32.5, 32.7 R

[56] References Cited

U.S. PATENT DOCUMENTS

| Re. 32,295 | 11/1986 | Braid | 252/32.7 E |
| 4,743,386 | 5/1988 | Doner | 252/32.7 E |
| 4,784,780 | 11/1988 | Farng | 252/32.7 E |

*Primary Examiner*—William R. Dixon, Jr.
*Assistant Examiner*—James M. Hunter, Jr.
*Attorney, Agent, or Firm*—Alexander J. McKillop; Charles J. Speciale; Howard M. Flournoy

[57] ABSTRACT

Hindered phenolic/phosphorodithioate-derived alcohol borates have been found to be effective multifunctional antioxidant/antiwear additives for lubricants and fuel.

31 Claims, No Drawings

LUBRICANT COMPOSITION CONTAINING PHENOLIC/PHOSPHORODITHIOATE BORATES AS MULTIFUNCTIONAL ADDITIVES

BACKGROUND OF THE INVENTION

This application is directed to the promotion of effective antioxidant and antiwear activity in various lubricants and liquid hydrocarbon fuels. More particularly this invention is directed to compositions containing multifunctional antioxidant/antiwear additives comprising hindered phenolic phosphorodithioate-derived alcohol borates and to the additives themselves.

The use of hindered phenolic compounds, such as di-tertiary butyl paracresol, for their antioxidant properties in a variety of lubricant, polymer and elastomer applications is well known.

The use of phosphorodithioates have found widespread use for several decades in engine oils as multifuctional antiwear and bearing corrosion inhibiting additives, for example ZnDTP.

The use of borate esters has been widely reported as having beneficial multifunctional friction reducing properties. Borate esters of hindered phenols are disclosed in U.S. Pat. No.3,347,783 and U.S. Pat. No. 3,359,298. Re 32,295 (November, 1986) discloses the use of the reaction products of (1) a hindered phenol, (2) a boron compound and an amine as having friction reducing fuel saving properties.

It has now been found that the use of hindered phenolic/phosphorodithioate-derived alcohol borates provide exceptional antioxidant and antiwear activity and additionally with potential corrosion inhibiting, antifatigue and high temperature stabilizing properties.

Accordingly, it is an object of the present invention to provide novel additive products, suitable for use as antioxidant and antiwear multifunctional additives in various lubricant media and liquid hydrocarbon fuels.

SUMMARY OF THE INVENTION

In accordance with the invention there is provided a product of reaction prepared by reacting a hindered phenol, a boron compound and a phosphorodithioate-derived alcohol. The invention also provides a lubricant composition comprising a major proportion of lubricant and a fuel composition comprising a major proportion of a liquid hydrocarbon fuel, and a minor multifunctional antioxidant/antiwear amount of said reaction product.

Lubricant compositions containing small additive concentrations of hindered phenolic/phosphorodithioate-derived-alcohol borates in accordance with the invention possess excellent antioxidant properties coupled with very good antiwear activity. Both the hindered phenolic moiety and the phosphorodithioate alcohol moiety are believed to provide the basis for the synergistic antioxidant activity each of which are subsequently enhanced by the integral boron coupling moiety. The phosphorodithioate group is believed to contribute additional antiwear properties to these novel additives. The boron moieties may additionally contribute significant antifatigue and/or high temperature stabilizing properties to this new class of additives.

All of these beneficial properties are believed to be enhanced as a result of novel internal synergism. This unique internal synergism concept is believed to be applicable to similar structures containing (a) hindered phenolic groups, (b) phosphorodithioate-derived alcohol groups and (c) borate ester linkages within the same molecule.

DESCRIPTION OF SPECIFIC EMBODIMENTS

The reaction products of this invention as noted here and above are made by reacting a boron compound, a hindered phenol, and a phosphorodithioate-derived alcohol. Preferably the reaction to form the additive product will take place in one stage. After preparation of the various components in any suitable manner, for example, O,O-dialkyl phosphorodithioic acids (made by the reaction of alcohols with phosphorus pentasulfide) were reacted with alkylene oxides to form phosphorodithioate-derived alcohols. These alcohols are then co-borated with hindered phenolic alcohols to form mixed borate esters, as generally exemplified below:

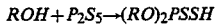

wherein R is $C_3$ to about $C_{30}$ hydrocarbyl or $C_3$ to about $C_{30}$ or hydrocarbyloxyhydrocarbylene, or mixtures thereof.

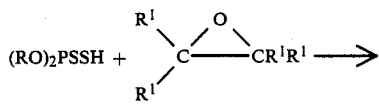

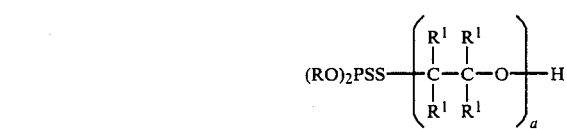

wherein a is 1–10, and each $R^1$ is independently hydrogen or $C_1$ to $C_{30}$ hydrocarbyl

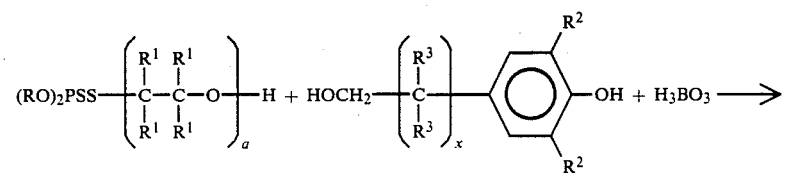

-continued

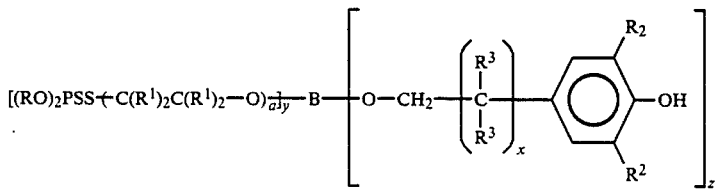

where each $R^1$ is independently hydrogen or $C_1$–$C_{30}$ hydrocarbyl and each $R_2$ and $R_3$ are independently hydrogen, or $C_1$–$C_{10}$ hydrocarbyl x is 0 to 10 y and z are integers and y+z=3 or

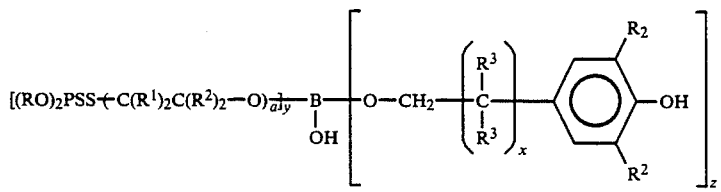

where $R^1$, $R^2$, $R^3$ and x are as defined above and y+z are integers which equal 2.

Hydrocarboxyl as used throughout the specification includes alkyl, alkenyl, etc. as more fully set forth herein below.

An excess of one reagent or another can be used. Molar qualities, less than molar quantities or more than molar quantities of a suitable boronating agent can be used. Boric acid can be used as a boronating agent or metaborates, trialkyl borates or any other suitable boronating agent may be employed. Thus a variety of methods are available for use in making the additives. The reactions can be carried out over a wide range of temperatures, i.e., from about 30° C. to 250° C. and preferably 90° C. to 150° C. The same relative proporations are used regardless of reaction temperature. Preferably the reactions take place under ambient pressure. However, higher pressure may be used if desired.

The hindered phenols that are contemplated herein have the formula

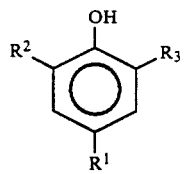

where $R^2$ and $R^3$ are the same or different alkyl group containing from 1 to about 18 carbon atoms, preferably from 1 to about 10 carbon atoms and preferably a tertiary alkyl group. Broadly, the carbon atoms of the alkyl group can be in any isomeric arrangement provided that the carbon atom bonded to the phenyl group is itself bonded to at least two other carbon atoms or chain segments, and $R^1$ is a hydroxy containing C. to $C_{30}$ hydrocarbyl group, i.e., an alkyl, alkenyl, cycloalkyl, aryl, aralkyl or alkaryl group which may have substituted thereon other groups, e.g., an alkoxy group, an alkylthio group or the like.

The hindered phenols include but are not limited to 2,6-di-t-butyl 4-hydroxymethylphenol, 2,6-di-sec-butyl 4-hydroxymethylphenol, and (3,5-di-t-butyl-4-hydroxy)dihydrocinnamyl alcohol and the like.

Of particular significance, in accordance with the present invention, is the ability to improve antiwear and oxidation and high temperature stabilizing properties of oleaginous materials such as lubricating media which may comprise either a mineral oil or a synthetic oil or mixtures thereof, or a grease therefrom. In general, mineral oils, both paraffinic, naphthenic oils and mixtures thereof, employed as the lubricating oil or grease vehicle, may be of any suitable lubricating viscosity range. For example, they may range in viscosities of from about 45 SSU at 100° F. to about 6000 SSU at 100° F, and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800.

In instances where synthetic oils or combinations thereof with mineral oils are preferred, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl) sebacate, di(2-ethylhexyl)adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones(polysiloxanes), alkyl-substituted diphenyl ethers typified by a butyl-substituted bis(p-phenoxy phenol) ether, phenoxy, phenylethers. It is to be understood, however, that the compositions contemplated herein can also contain other materials. For example, corrosion inhibitors, extreme pressure agents, viscosity index improvers, co-antioxidants, anti-wear agents and the like can be used, including metal phenates, e.g. calcium or magnesium alkyl phenates, metal sulfonates, e.g. calcium or magnesium aryl sulfonates and zinc phosphorodithioates, i.e., zinc dihydrocarbyl phosphorodithioates. These can be used in amounts in total of from about 0.1% to about 5% by weight, preferably from about 0.5 to about 2% by weight. These materials do not detract from the value of the compositions of this invention, but rather they serve to impart their customary priorities to the particular compositions in which they are incorporated. In general, the preformed adducts of the present invention may be employed in any amount which is effective for imparting the desired degree of friction reduction anti-corrosion or anti-wear activity In many applications, however, the adduct is effectively employed in amounts from about 0.1% to about 10% by weight, preferably from about 0.5 to about 5% of the total weight of the composition.

With respect to the greases of the invention, a wide variety of thickening agents can be used to prepare them. Included among the useful thickening agents are alkali and alkaline earth metal soaps of fatty acids and fatty materials having from about 12 to about 30 carbon atoms per molecule. The metals are typified sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065) calcium caprylate-acetate (U.S. Pat. No. 2,999,066), and calcium salts and soaps of low-, intermediate-and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an ammonium compound. Typical ammonium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These can be described as complex inorganic silicates such as aluminum silicates, magnesium silicates, barium silicates, and the like, containing, in addition to the silicate lattice, varying amount of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15, percent by weight of the total grease composition.

The borate compounds in accordance with the invention can be employed in any amount sufficient to impart the desired degree of protection against oxidative degradation. In many instances the additives can be employed in amounts up to about 10% by weight but preferably from about 0.01 to about 5% by weight and more preferably from about 0.1-0.5 to about 2% by weight of the total composition.

These additives can be used in conjunction with standard additive packages without hindering the ability of such additives to perform their intended functions. For example, these additives can be used with polymeric dispersants, metallic phenate or sulfonate detergents, zinc, phosphorus and/or sulfur containing antiwear additives, polymeric VI improvers, defoamants and corrosion inhibitors.

The liquid fuels contemplated included liquid hydrocarbon fuels such as fuel oils, diesel oils and gasolines and alcohol fuels such as xethanol and ethanol or mixtures of these fuels. The effective amount of additive therein for fuel use reduction will range from about 5 pounds to about 1,000 pounds thereof per 1,000 barrels of fuel, preferably from about 20 pounds to about 50 pounds per 1,000 barrels.

The following Examples will present illustrations of the invention. They are illustrative only, and are not meant to limit the invention. Parts are by weight.

EXAMPLES

EXAMPLE 1

Propoxylated Di-2-Ethylhexylphosphorodithioic Acid

Approximately 708.6 grams of di-2-ethylhexylphosphorodithioic acid was commercially obtained and charged into a one liter flask and slowly 116.2 grams (2.0 mole) propylene oxide was added over a course of two hours. The reaction temperature was controlled at below about 40° C. by using ice-water bath for cooling. At the end of the addition, the mixture changed its color from dark-greenish to light-yellowish. It weighed approximately 825 grams.

EXAMPLE 2

Hindered Phenolic Alcohol/Propoxylated Di-2-Ethylhexylphosphorodithioic Acid Mixed Borate Approximately 206.3 grams of the above product of Example 1, 59 grams of 2-6-di-tertiary-butyl-4-hydroxymethylohenol, commercially obtained, 15.5 grams boric acid (0.25 mole), 200 milliliters toluene were mixed together in a one liter, four-neck reactor equipped with thermometer, $N_2$ sparger, and Dean-Stark trap condenser and agitator. This mixture was refluxed at boiling toluene (113±2° C.) over a course of three hours. A total amount of 12.8 milliliters of water was collected in the Dean-Stark trap.

An additional hour of heating produced no more water of reaction. The toluene was removed by distillation to produce about 274 grams of a low-viscosity reddish-brown liquid.

The hindered phenolic/phosphorodithioate-derived alcohol borates were blended into fully formulated oils and evaluated for both antioxidant performance and antiwear activity as shown below.

EVALUATION OF PRODUCTS CATALYTIC OXIDATION TEST

The products of the examples were blended into fully formulated oils and evaluated by, Catalytic Oxidation Test at 325° F. for 40 hours (Table 1); Catalytic Oxidation Test at 260° F. for 80 hours (Table 2); and Catalytic Oxidation Test at 375° F. for 24 hours (Table 3).

The test lubricant composition is subjected to a stream of air which is bubbled through the composition at a rate of 5 liters per hour at 325° F. for 40 hours (260° F. for 80 hours and 375° F for 24 hours). Present in the composition are metals commonly used as materials of engine construction, namely:

(a) 15.6 square inch of sand-blasted iron wire,
(b) 0.78 square inch of polished copper wire,
(c) 0.87 square inch of polished aluminum wire, and
(d) 0.167 square inch of Polished lead surface.

Inhibitors for oil are rated on the basis of prevention of oil deterioration as measured by the increase in acid formation or neutralization number ($\Delta$NN) and kinematic viscosity ($\Delta$KV) occasioned by the oxidation. Compounds in accordance with this invention tested for their oxidative stabilizing properties in accordance with the above Catalytic Oxidation Test proved highly effective oxidation stabilizers and/or inhibitors.

In assessing the results of this test, it will be understood that the more important consideration is the control of viscosity increase ($\Delta$KV).

TABLE 1

Catalytic Oxidation Test (325° F., 40 Hours)

| Item | Additive Conc. (Wt. %) | Percent Change in Acid Number $\Delta$ TAN | Percent Change in Viscosity $\Delta$ KV | Sludge |
|---|---|---|---|---|
| Base Oil (150 second, fully formulated, solvent refined paraffinic bright oil containing defoamant/demulsifier/antiwear/anticorrosion/EP/antirust performance package | — | 2.58 | 30.62 | Nil |
| Example 2 | 1.0 | 2.53 | 27.36 | Light |

TABLE 2

Catalytic Oxidation Test (260° F., 80 Hours)

| Item | Additive Conc. (Wt. %) | Percent Change in Acid Number $\Delta$ TAN | Percent Change in Viscosity $\Delta$ KV | Sludge |
|---|---|---|---|---|
| Base Oil (150 second, fully formulated, solvent refined paraffinic bright oil containing defoamant/demulsifier/antiwear/anticorrosion/EP/antirust performance package | — | 0.01 | 6.48 | Nil |
| Example 2 | 1.0 | −0.12 | 5.85 | Nil |

TABLE 3

Catalytic Oxidation Test (375° F., 24 Hours)

| Item | Additive Conc. (Wt. %) | Percent Change in Acid Number $\Delta$ TAN | Percent Change in Viscosity $\Delta$ KV | Sludge |
|---|---|---|---|---|
| Base Oil (150 second, fully formulated, solvent refined paraffinic bright oil containing defoamant/demulsifier/antiwear/anticorrosion/EP/antirust performance package | — | 6.53 | 177.9 | Medium |
| Example 2 | 1.0 | 3.90 | 125.2 | Light |

As shown above, the products of this invention show very good antioxidant activity as evidenced by control of increase in acidity and viscosity.

The hindered phenolic/phosphorodithioate-derived alcohol borates were also evaluated for antiwear performance using the Four-Ball Test, see Table 4.

The Standard Four-Ball Test is disclosed in, for example, U.S. Pat. No. 3,423,316. In general, in this test three steel balls of 52-100 steel are held in a ball cup. A fourth ball positioned on a rotatable vertical axis is brought into contact with the tree balls and is rotated against them. The force with which the fourth ball is held against the three stationary balls may be varied according to a desired load. The test lubricant is added to the ball cup and acts as a lubricant for the rotation. At the end of the test, the steel balls are investigated for wear scar; the extent of scarring represents the effectiveness of the lubricant as an antiwear agent (Table 2).

TABLE 4

| | Wear Scar Diameter in mm, 30 Minute Test - 60 kg Load | | | |
|---|---|---|---|---|
| Item | 1000 RPM 200° F. | 2000 RPM 200° F. | 1000 RPM 300° F. | 2000 RPM 300° F. |
| Base Oil (80% Solvent Paraffinic Bright, 20% Solvent Paraffinic Neutral Mineral Oils) | 1.91 | 2.63 | 1.95 | 2.50 |
| 1% Example 2 in above Base Oil | 0.82 | 1.06 | 0.88 | 1.14 |

As can be seen from the above wear test results, the products described exhibit considerable antiwear activity.

It is apparent from the data of Tables 1, 2, 3, and 4 that the additive products of the present invention are markedly effective not only as oxidation stabilizers but also as antiwear additives in lubricant oils.

While this invention has been described with reference to preferred compositions and components therefor, it will be understood by those skilled in the art that departure form the preferred embodiments can be effectively made and are within the scope of the present specification.

We claim

1. A lubricant composition comprising a major amount of an oil of lubricating viscosity or grease or other solid lubricant prepared therefrom and a minor effective multifunctional antioxidant and antiwear improving amount of an additive compound of a hindered phenolic phosphorodithioate-derived alcohol borate obtained by co-boronating said phosphorodithioate-derived alcohol with a hindered phenolic alcohol to form a mixture of borate esters at least a portion of which has one or more of the following general structures:

$$[(RO)_2PSS + C(R^1)_2C(R^1)_2 - O]_{\overline{a}y} - B -$$

$$\left[ -O-CH_2 - \left( \begin{array}{c} R^3 \\ | \\ C \\ | \\ R^3 \end{array} \right)_x - \left\langle \begin{array}{c} R^2 \\ \\ \\ R^2 \end{array} \right\rangle - OH \right]_z$$

wherein a=1 to 10 and where R is $C_3$ to about $C_{30}$ hydrocarbyl, $R^1$ is hydrogen or $C_1$-$C_{30}$ hydrocarbyl, $R^2$ and $R^3$ are each independently hydrogen, or $C_1$-$C_{10}$ hydrocarbyl,
x is 0 to 10,
y and z are integers and y+z=3 or or $$[(RO)_2PSS + C(R^1)_2C(R^1)_2 - O]_{\overline{a}y} - B - \\ | \\ OH$$

$$\left[ -O-CH_2 - \left( \begin{array}{c} R^3 \\ | \\ C \\ | \\ R^3 \end{array} \right)_x - \left\langle \begin{array}{c} R^2 \\ \\ \\ R^2 \end{array} \right\rangle - OH \right]_z$$

where a=1 to 10 and where x, y, z, R, $R^1$, $R^2$, and $R^3$ are as defined above and y+z are integers the sum of which=2.

2. The lubricant of claim 1 containing one or more additives chosen from the group consisting of polymeric dispersants, metallic phenate additives or sulfonate detergents, zinc, phosphorus, sulfur or, phosphorus and sulfur containing antiwear additives, polymeric viscosity index improvers, defoamants, and corrosion inhibitors.

3. The lubricant composition as defined in claim 1 wherein the additive product is present in an amount of from about 0.01 to about 10% by weight of a said composition.

4. The lubricant composition as defined in claim 1 wherein the additive product is present and in amount about from about 0.01 to about 5% by weight of a said composition.

5. The composition of claim 1 wherein the additive product is a hindered phenolic alcohol/propoxylated di-2-ethylhexyl-phosphorodithioic acid mixed borate.

6. The composition of claim 5 wherein the hindered phenolic alcohol is 2-6-ditertiary-butyl-4-hydroxymethylphenol.

7. The lubricant composition defined in claim 1 wherein said lubricant is selected from mineral oils or fractions thereof, synthetic oils or mixtures of mineral and synthetic oils.

8. The lubricant composition defined in claim 3 wherein said lubricant is selected from mineral oils or fractions thereof, synthetic oils or mixtures of mineral and synthetic oils.

9. The lubricant composition defined in claim 5 wherein said lubricant is selected from mineral oils or fractions thereof, synthetic oils or mixtures of mineral and synthetic oils.

10. The lubricant composition defined in claim 6 wherein said lubricant is selected from mineral oils or fractions thereof, synthetic oils or mixtures of mineral and synthetic oils.

11. The lubricant composition of claim 7 wherein the lubricant is a mineral oil.

12. The lubricant composition of claim 8 wherein the lubricant is a mineral oil.

13. The lubricant composition of claim 9 wherein the lubricant is a mineral oil.

14. The lubricant composition of claim 10 wherein the lubricant is a mineral oil.

15. The lubricant composition of claim 7 wherein the lubricant is a synthetic oil.

16. The lubricant composition of claim 8 wherein the lubricant is a synthetic oil.

17. The lubricant composition of claim 9 wherein the lubricant is a synthetic oil.

18. The lubricant composition of claim 10 wherein the lubricant is a synthetic oil.

19. The composition of claim 1 wherein said lubricant is a grease.

20. The composition of claim 19 wherein said grease is thickened with a metal hydroxyl-containing carboxylate thickener.

21. The composition of claim 7 wherein said lubricant is a grease.

22. The composition of claim 3 wherein said lubricant is a grease.

23. The composition of claim 5 wherein the lubricant is a grease.

24. The composition of claim 6 wherein the lubricant is a grease.

25. An additive product suitable for use in lubricant compositions having improved antioxidant and antiwear properties prepared by reacting a hindered phenol, a phosphorodithioic-derived alcohol and a boronating compound.

26. The additive product of claim 25 containing one or more of the following generalized structures:

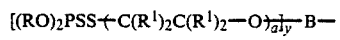

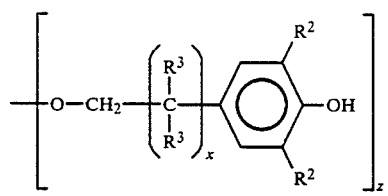

where a=1 to 10 and where R is $C_3$ to about $C_{30}$ hydrocarbyl, and each $R^1$ is independently hydrogen or $C_1$–$C_{30}$ hydrocarbyl, and each $R^2$ and $R^3$ are independently hydrogen, or $C_1$–$C_{10}$ hydrocarbyl, x is 0 to 10 y and z are integers and y=z=3 or

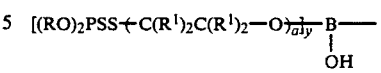

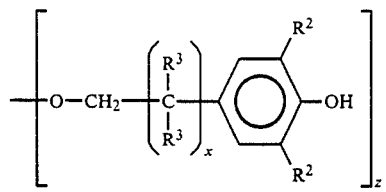

where a=1 to 10 and where R, $R^1$, $R^2$, $R^3$ and x are as defined above and y +z are integers the sum of which=2.

27. The additive product of claim 25 wherein the hindered phenolic reactant is selected from the group consisting of 2,6-di-tert-butyl 4-hydroxymethylphenol 2,6-di-sec-butyl 4-hydroxymethylphenol and (3,5-di-t-butyl-4-hydroxyocinnamyl alcohol.

28. The additive product claim 21 wherein the phosphorodithioate component is derived from the group consisting of methyl, ethyl, propyl, iosopropyl, 2-ethylhexyl, 4-methyl-2-pentyl, isodecyl, tetradecyl and octadecyl phosphorodithioates.

29. The additive product of claim 28 wherein said phosphorodithioate component is 2-ethyltexylphosphorodithioic acid.

30. The additive product of claim 25 wherein said product is a hindered phenolic alcohol propoxylated di-2-ethylhexylphosphorodithioic acid mixed borate.

31. The additive product of claim 30 wherein said hindered phenolic alcohol is 2-6-ditertiary-butyl-4-hydroxyxethyl-phenol.

* * * * *